US 6,564,156 B2

(12) United States Patent
Kuo et al.

(10) Patent No.: US 6,564,156 B2
(45) Date of Patent: May 13, 2003

(54) METHOD FOR DETERMINING JOINT STIFFNESS DEGRADATION

(75) Inventors: Everett You-Ming Kuo, Troy, MI (US); A. Mangala Mahinda Jayasuriya, Bloomfield Hills, MI (US); Efstratios Nikolaidis, Blacksburg, VA (US); Richardo Anibal Burdisso, Blacksburg, VA (US)

(73) Assignee: Ford Global Technologies, Inc., Dearborn, MI (US)

( * ) Notice: Subject to any disclaimer, the term of this patent is extended or adjusted under 35 U.S.C. 154(b) by 2 days.

(21) Appl. No.: 09/805,077

(22) Filed: Mar. 13, 2001

(65) Prior Publication Data

US 2002/0161531 A1 Oct. 31, 2002

(51) Int. Cl.$^7$ ................................................. G01B 5/28
(52) U.S. Cl. ............................. 702/36; 702/34; 702/36; 700/30; 700/31; 73/588; 73/602; 73/788
(58) Field of Search ............................... 702/36, 56, 34; 700/30, 31; 73/570, 579, 582, 583, 584, 588, 594, 602, 669, 760, 763, 785, 786, 788, 789, 802, 804, 805, 808

(56) References Cited

U.S. PATENT DOCUMENTS

| 4,033,182 A | 7/1977 | Cotfelter |
| 4,694,698 A | 9/1987 | Miyajima |
| 4,901,575 A | * 2/1990 | Bohannan et al. ............. 73/587 |
| 4,979,394 A | 12/1990 | Higo et al. |
| 5,327,358 A | * 7/1994 | Stubbs ......................... 702/36 |
| 5,418,858 A | * 5/1995 | Shoureshi ................. 381/71.12 |
| 5,421,206 A | 6/1995 | Rohwedder |
| 5,569,857 A | 10/1996 | Miyazaki |
| 5,610,837 A | 3/1997 | Murphy |
| 5,723,792 A | 3/1998 | Miyazaki |
| 5,886,263 A | * 3/1999 | Nath et al. ..................... 700/30 |
| 6,199,431 B1 | * 3/2001 | Nath et al. ..................... 73/579 |

* cited by examiner

Primary Examiner—John Barlow
Assistant Examiner—Stephen J. Cherry
(74) Attorney, Agent, or Firm—Gigette M. Bejin

(57) ABSTRACT

A method of determining joint stiffness degradation in structure 10 is provided including a first exciting of the structure 18, a first measuring of transfer function and frequency response function 20, simulating a mileage accumulation process of the structure 16 performed after the first exciting 18 and the first measuring 20, a second exciting of the structure 22, performed after the simulating a mileage accumulation process 16, a second measuring of frequency response function 24 performed after the simulating a mileage accumulation process 16 and calculating the change in joint stiffness 26 using the first measuring 20 and the second measuring 24.

15 Claims, 2 Drawing Sheets

METHOD FOR DETERMINING JOINT STIFFNESS DEGRADATION

TECHNICAL FIELD

The present invention relates generally to a method for determining joint stiffness degradation and more particularly to a non-destructive method for determining joint stiffness degradation.

BACKGROUND OF THE INVENTION

NVH (noise, vibration, and harshness) performance can be a major concern in many product designs. Many products, such as automobiles, may experience NVH degradation over the life of the product. This degradation may result from a combination of age and use (mileage in the case of automobiles). NVH degradation can result in a reduction of product performance and customer satisfaction. This is highly undesirable.

In the case of automotive designs, one cause of high mileage NVH degradation is a loss of joint stiffness. The loss of joint stiffness from the body structure can result from fatigue, loosening, aging, wear, corrosion, and a host of other causes. In order to design vehicles with reduced NVH degradation, it often is important to analyze designs to determine locations of body joint stiffness degradation due to high mileage. By isolating such positions, joint stiffness may be modified and improved to avoid future NVH degradation.

Conventional test methods for determining joint stiffness typically require cutting the joints off a vehicle body. Stiffness degradation of each joint is determined by the difference of stiffness before and after mileage accumulation. Since the test requires destroying the vehicle body by cutting off the joints, at least two vehicles are required (one for initial testing and a second after mileage accumulation) adding to the time and cost of the test. In addition, the process of cutting the joints off the vehicle body and performing conventional joint stiffness tests can also be an expensive and time-consuming procedure. Finally, since the conventional procedure requires separate vehicles to be cut and tested for a low versus high mileage stiffness testing, the potential for significant variabilities in both the cut joints and testing procedures are possible. This may result in unreliable stiffness degradation predictions. A test procedure that could be performed non-destructively on a single vehicle body before and after mileage accumulation could reduce expenses, reduce time for testing, and increase testing accuracy. While it is possible to use standard body modal and static bending/torsion stiffness tests to determine the reduction in overall body stiffness and natural frequency due to high mileage, these tests do not identify local joint stiffness degradation which can be crucial in the prediction and prevention of high mileage NVH degradation.

It would, therefore, be highly desirable to have a non-destructive method for determining joint stiffness degradation. It would further be highly desirable to have a method for determining joint stiffness degradation that reduce the expense and time often associated with such procedures. Finally, it would be desirable to have a method for determining joint stiffness degradation that could potentially reduce testing variabilities.

SUMMARY OF THE INVENTION

It is, therefore, an object of the present invention to provide a method for determining joint stiffness degradation that is non-destructive, can reduce the time and cost of testing, and reduce hardware test variabilities.

In accordance with the objects of the present invention, a method for determining joint stiffness degradation is provided. The method includes a first exciting of the structure and a first measuring of transfer function and frequency response function. The method also includes simulating a mileage accumulation process of the structure. After the mileage accumulation process of the structure, a second exciting of the structure and a second measuring of frequency response function is undertaken. The first measuring and the second measuring are then used to calculate change in joint stiffness.

Other objects and features of the present invention will become apparent when viewed in light of the detailed description of the preferred embodiment when taken in conjunction with the attached drawings and the appended claims.

DESCRIPTION OF THE PREFERRED EMBODIMENT(S)

Figure 1:
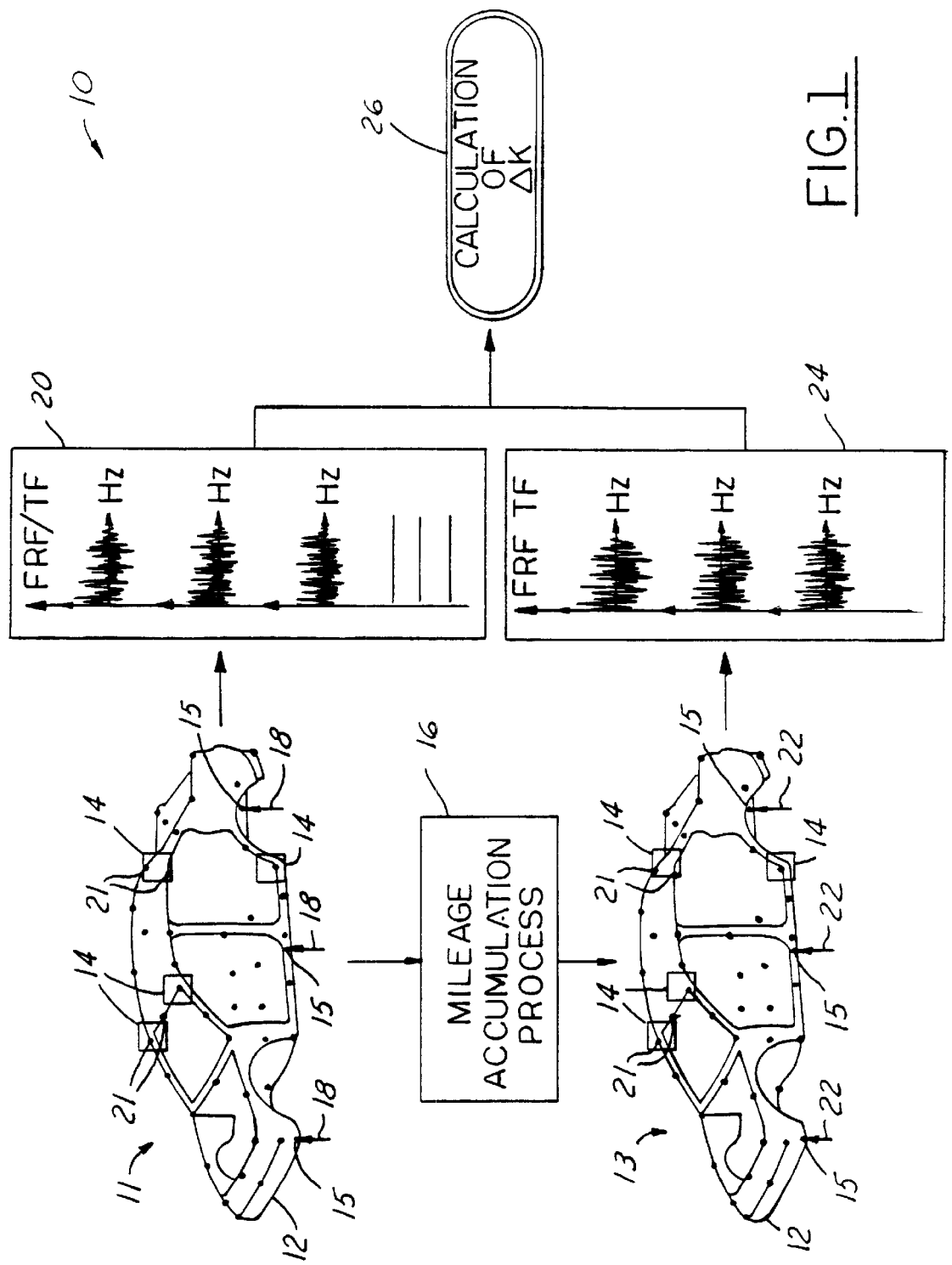
FIG. 1 is an illustration of an embodiment of a method for determining joint stiffness degradations in accordance with the present invention.

Referring now to FIG. 1, which is an illustration of an embodiment of a method for determining joint stiffness degradation 10 in accordance with the present invention. The method for determining joint stiffness degradation 10 is intended for use on a structure 12, such as an automobile, containing at least one joint 14 location, or other localized stiffness area to be investigated(numerous examples of individual joints 14 are illustrated). The method for determining joint stiffness degradation 10 is useful in determining changes in stiffness of the structure 12 by comparing the zero-mileage structure 11 with the accumulated mileage structure 13 having been subjected to a mileage accumulation process 16.

The method of determining joint stiffness degradation 10 includes a first exciting 18 of the structure 12. The first exciting 18 may be applied to the structure 12 in a single location or a plurality of locations. A variety of methods of exciting structures are well known in the prior art. The method of determining joint stiffness degradation 10 further includes a first measuring of transfer function and frequency response function 20. The selection of joints 14 and the identification of joint nodes 21 may be done at a single location, or in a variety of locations.

The first measuring 20, performed on the zero mileage structure 11, includes measuring the transfer function (TF) between the joint nodes 21 and response points 15. The first measuring 20 also includes measuring the frequency response function (FRF) at the joint nodes 21, in response to the first exciting 18. The TF is determined by applying unit dynamic loads at the response points 15. It should be understood that in a typical modal test, the locations for the first exciting 18 may be identical to the response points 15, although this is not required. Although a variety of known methods may be utilized to measure the TF and the FRF, one known method utilizes tri-axial accelerometers (not shown) positioned at the joint nodes 21, the position of the first exciting 18, and the response points 15. The use of tri-axial accelerometers (not shown) or other sensors to measure TF and FRF is well known in the prior art.

After the first measuring 20, the structure 12 is subjected to simulating a mileage accumulation process 16. The mileage accumulation process 16, also referred to as durability loading, is intended to encompass a wide variety of situations in which the stiffness of the structure 12 and its joints 14 may be affected. In a preferred embodiment, the mileage accumulation process 16 is an accelerated mileage accumulation equivalent to several years of service on the road. This accelerated mileage accumulation is commonly intended to expose the structure 12 to the loading and stresses typically experienced over its lifetime. This may include, but is not limited to, atypical loading, temperature fluctuation and vibrational loading. This process is well known in the prior art. Although the term "mileage" has been used, it should be understood that the mileage accumulation process is intended to include any process that may vary the stiffness of the structure 12 or its joints The process of exciting a structure 18 and measuring transfer function and frequency response 20 is a known and common procedure in engineering analysis. After the first measuring 20, the vehicle 12 is subjected to simulating a mileage accumulation process 16 as previously discussed. After the mileage accumulation process 16, a second exciting of the structure 22 is performed and a second measuring of frequency response function 24 is made.

The first measuring 20 and the second measuring 24 are then utilized to calculate the change in joint stiffness 26. The method of determining joint stiffness 10 is performed after developing regression models using joint stiffness degradation parameters, TF and FRF data. These regression models are comprised of complex value over-determinate matrices which can be solved by using a prior developed method such as Kuhn-Tucker condition.

Figure 2:
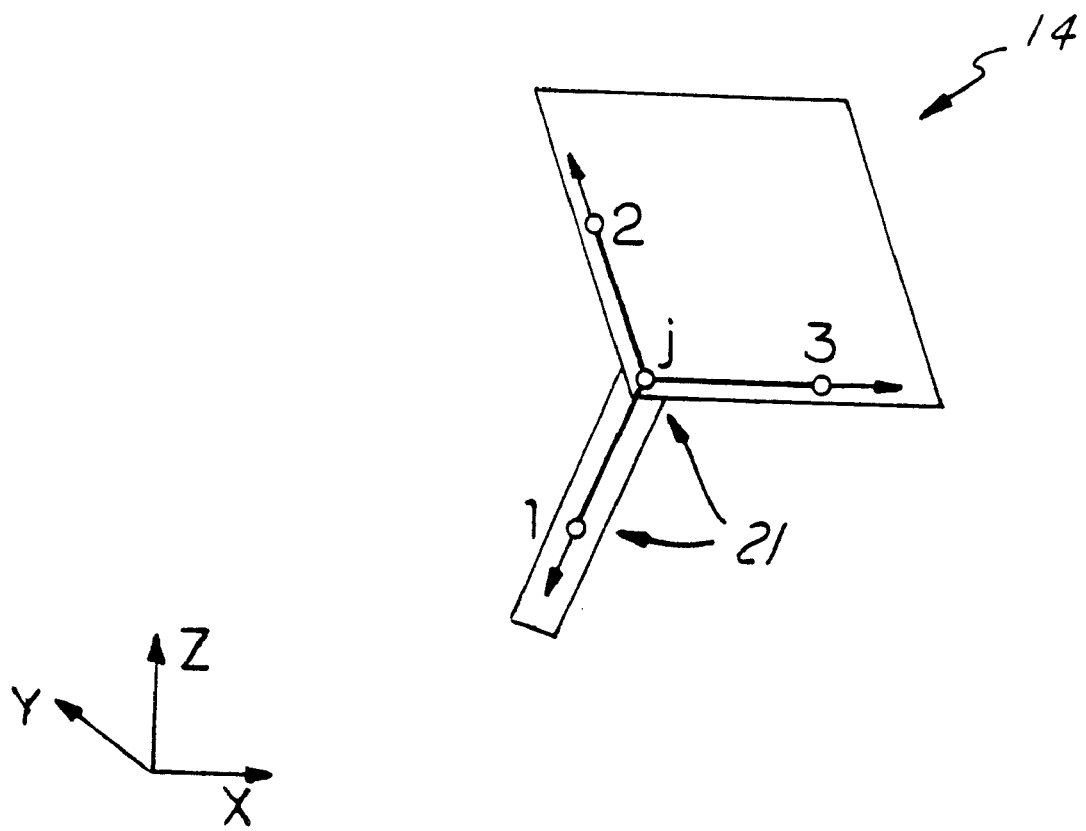
FIG. 2 is an illustration of a model of a joint in accordance with the present invention.

Referring now to FIG. 2 which is a model of a joint in accordance with the present invention. In this invention, the stiffness degradation is expressed as:

$$\{U_m\}-\{\hat{U}_m\}=[d_{mj}][K]\{\hat{U}_j\}$$

where $\{U_m\}$ is the measured FRF at the response points of the zero-mileage vehicle structure $\{\hat{U}_m\}$ is the measured FRF at the response points of the high-mileage vehicle structure $[d_{mj}]$ is a dynamic compliance matrix calculated using the TF between joint nodes and response points $[K]$ is the joint stiffness degradation matrix that derived from 3-parameter beams as shown in FIG. 2.

$\{\hat{U}_j\}$ is the FRF at the joint nodes of the high-mileage vehicle structure This equation can be interpreted by the following expression, $$\begin{pmatrix} \text{The difference in FRF} \\ \text{between zero mileage and} \\ \text{high mileage structure} \end{pmatrix} = \sum_{joints} \begin{pmatrix} \text{Sensitivity of change} \\ \text{in response w.r.t.} \\ \text{changes at joint} \end{pmatrix} \times \begin{pmatrix} \text{Stiffness} \\ \text{change} \\ \text{at joint} \end{pmatrix}$$

The above equation is written in the from of a linear regression model that leads to an over-determined complex value set of equations which can be solved by using the Kuhn-Tucker condition and a non-negative least squares method.

It should be noted that FIG. 1 shows a plurality of joint nodes 21 making measurements (20, 24) for a plurality of joints 14 at once. It should be understood that the present invention can determine the degradation of joint stiffness 10 for a single joint 14, although the degradation may be calculated for multiple joints simultaneously. In addition, although the term joint has been used throughout this application, it is contemplated that the present invention may be utilized to determine the stiffness degradation of any localized area within a structure and should not be limited strictly to areas fitting the designation of joints.

Since the structure 12 need not be disassembled or cut using the present invention in order to determine joint stiffness degradation, the present invention provides advantages over destructive testing methods. In addition, because such destructive methods are not required, the present invention may realize cost and time savings over prior methods. Finally, since only a single structure 12 is required for testing (as opposed to the two often required in destructive testing) variabilities in testing may be reduced. In addition, since the present invention does not adversely affect the structure 12 during testing, further simulating a mileage accumulation processes 16 and further determination of joint stiffness degradation 10 may be performed on the same structure 12.

While the invention has been described in connection with one or more embodiments, it is to be understood that the specific mechanisms and techniques which have been described are merely illustrative of the principles of the invention, numerous modifications may be made to the methods and apparatus described without departing from the spirit and scope of the invention as defined by the appended claims.

What is claimed is:

1. A method for determining joint stiffness degradation in a structure comprising:

applying a first excitation to the structure;

measuring a first transfer function using triaxial accelerometers and a first frequency response function;

simulating a mileage accumulation process of the structure;

applying a second excitation to the structure;

measuring a second frequency response function using triaxial accelerometers; and calculating the change in joint stiffness using measurements from the first transfer function, the first frequency response function, the second frequency response function, and a joint stiffness degradation matrix derived from three parameter beams.

2. A method of determining joint stiffness degradation in a structure as described in claim 1 wherein the step of applying a first excitation to the structure includes exciting the structure in a plurality of locations.

3. A method of determining joint stiffness as described in claim 1, wherein step of calculating the change in joint stiffness includes using the Kuhn-Tucker condition.

4. A method of determining joint stiffness degradation in a structure as described in claim 1 wherein the step of simulating a mileage accumulation process includes durability loading.

5. A method of determining joint stiffness degradation in a structure as described in claim 1 further comprising the steps of:

simulating a secondary mileage accumulation process performed after the steps of applying the second excitation to the structure and the step of measuring the second frequency response;

applying a third excitation to the structure performed after the step of simulating a secondary mileage accumulation process; and measuring a third frequency response function performed after.

6. A method of determining joint stiffness degradation in a structure as described in claim 1, wherein said calculating utilizes a non-negative least square method.

7. A method of determining joint stiffness degradation in a structure as described in claim 1, wherein said calculating utilizes a linear regression model.

8. A method of determining localized stiffness degradation in a structure as described in claim 5 wherein the step of simulating a mileage accumulation process of the structure includes durability loading.

9. A method of determining localized stiffness degradation in a structure as described in claim 5 further comprises the steps of:

simulating a secondary mileage accumulation process of the structure performed after said secondary exciting and said secondary measuring;

applying a third excitation to the structure performed after said simulating a secondary mileage accumulation process; and measuring a third localized frequency response.

10. A method for determining localized stiffness degradation in a structure comprising the steps of:

applying a first excitation to the structure;

measuring a first localized, transfer function and a first frequency response using triaxial accelerometers;

simulating a mileage accumulation process of the structure to be performed after applying the first excitation and measuring the first localized transfer function and the first frequency response;

applying a second excitation to the structure;

measuring a second localized frequency response using triaxial accelerometers; and calculating the change in localized stiffness using said first measuring, said second measuring, and a joint stiffness degradation matrix derived from three parameter beams.

11. A method of determining localized stiffness degradation in a structure as described in claim 10 wherein the step of applying a first excitation to the structure includes exciting the structure in a plurality of locations.

12. A method of determining localized stiffness degradation in a structure as described in claim 10 wherein the step of measuring a first localized transfer function and a first frequency response first measuring includes measuring in a plurality of locations.

13. A method of determining joint stiffness as described in claim 10, wherein the step of calculating the change in joint stiffness uses the Kuhn-Tucker condition.

14. A method of determining joint stiffness degradation in a structure as described in claim 10, wherein said calculating utilizes a non-negative least square method.

15. A method of determining joint stiffness degradation in a structure as described in claim 10, wherein said calculating utilizes a linear regression model.

* * * * *